(12) United States Patent
Ahn et al.

(10) Patent No.: US 12,324,609 B2
(45) Date of Patent: Jun. 10, 2025

(54) ADJUSTABLE SPINAL PLATE

(71) Applicant: AEGIS SPINE, INC., Englewood, CO (US)

(72) Inventors: Youngbo Ahn, Englewood, CO (US); Sungak Choi, Englewood, CO (US); Sangsoo Lee, Englewood, CO (US); Geungrok Kim, Englewood, CO (US); Jongwon Hong, Englewood, CO (US)

(73) Assignee: AEGIS SPINE, INC., Englewood, CO (US)

( * ) Notice: Subject to any disclaimer, the term of this patent is extended or adjusted under 35 U.S.C. 154(b) by 352 days.

(21) Appl. No.: 17/963,327

(22) Filed: Oct. 11, 2022

(65) Prior Publication Data

US 2024/0115297 A1 Apr. 11, 2024

(51) Int. Cl.
*A61B 17/80* (2006.01)
*A61B 17/70* (2006.01)

(52) U.S. Cl.
CPC ...... *A61B 17/7059* (2013.01); *A61B 17/8042* (2013.01)

(58) Field of Classification Search
CPC . A61B 17/80; A61B 17/8023; A61B 17/8042; A61B 17/8061; A61B 17/7059
See application file for complete search history.

(56) References Cited

U.S. PATENT DOCUMENTS

| 11,129,650 B1* | 9/2021 | Villamil ............. A61B 17/7058 |
| 2013/0060283 A1 | 3/2013 | Suh et al. |
| 2018/0235671 A1 | 8/2018 | Jackson, III |

* cited by examiner

*Primary Examiner* — Si Ming Ku
(74) *Attorney, Agent, or Firm* — WHDA, LLP

(57) ABSTRACT

The present invention provides a spinal plate which is used to perform fixation surgery on a spine in orthopedic surgery and neurosurgery. According to the present invention, a rotation device and a locking device may be installed so as to be used by fixing any one or more of longitudinal ends of the plate with being rotated at any angle, thereby allowing a doctor to modify a shape of the spinal plate to the shape desired by the doctor, and to perform the surgery by coping with various spin shapes of patients. In addition, according to the present invention, since the shape of the spinal plate may be rotated at any angle, it is possible to cope with various spin shapes of the patients.

3 Claims, 3 Drawing Sheets

[FIG. 1]
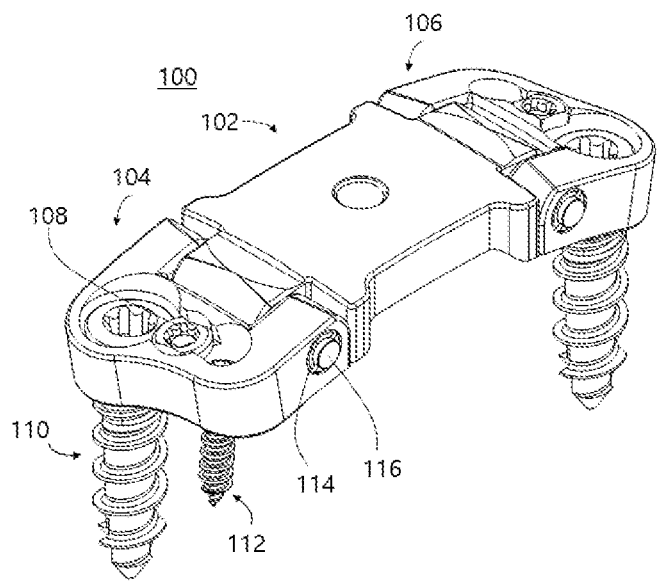
[FIG. 2]
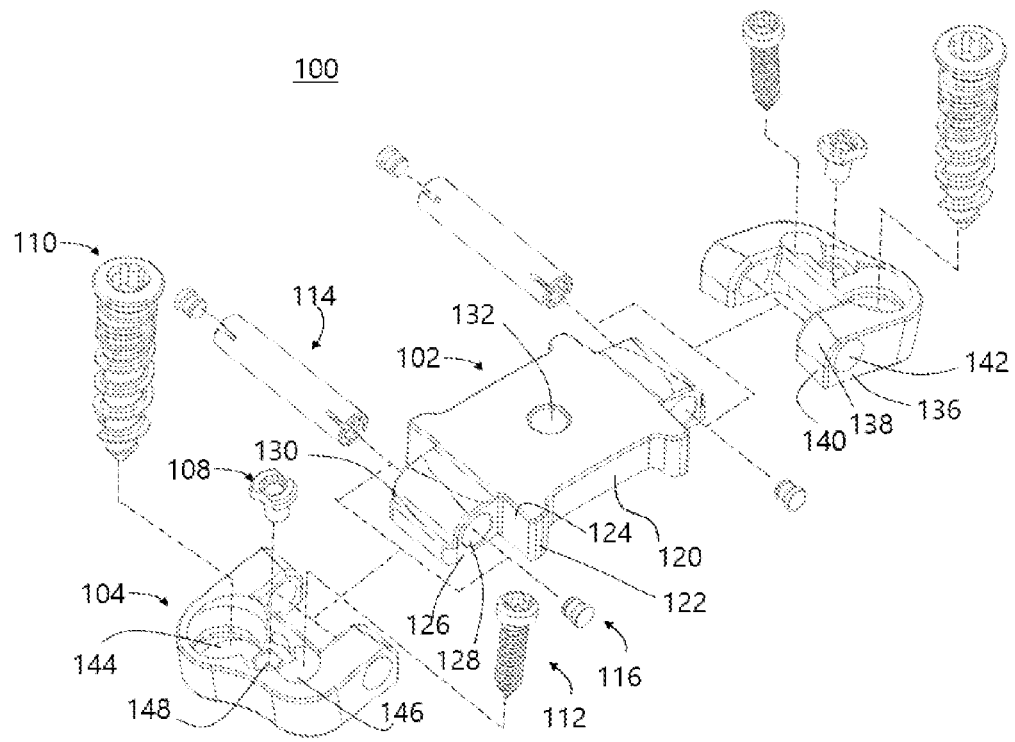

[FIG. 3]
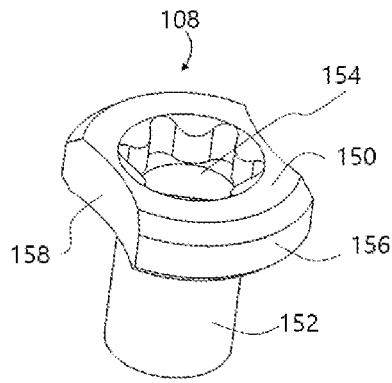
[FIG. 4]
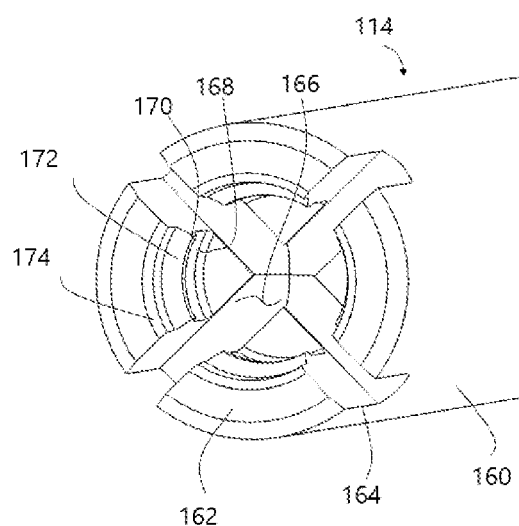
[FIG. 5]
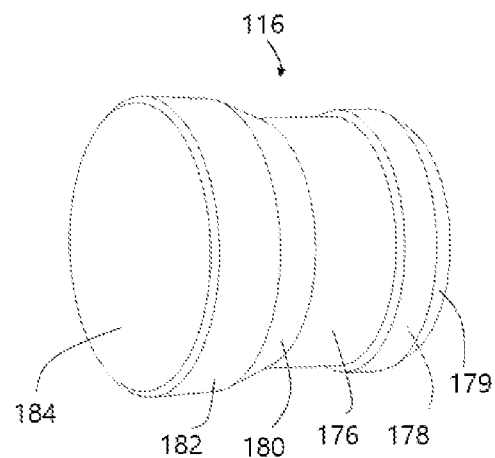

[FIG. 6]
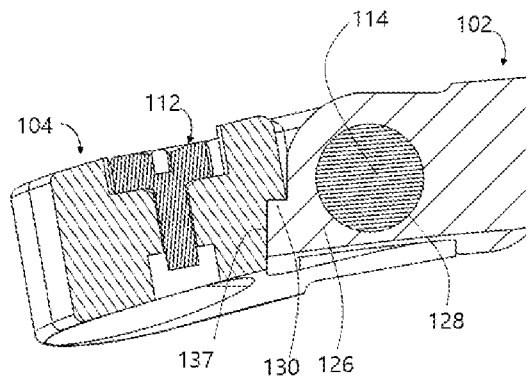
[FIG. 7]
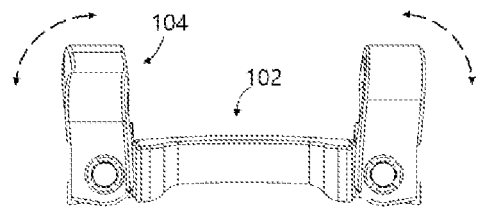
[FIG. 8]
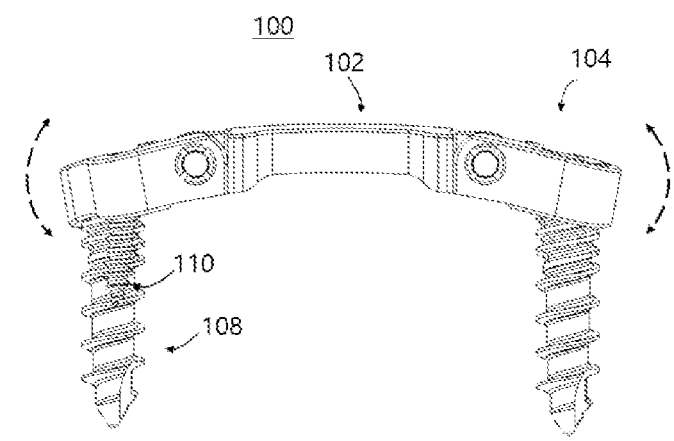

ADJUSTABLE SPINAL PLATE

BACKGROUND OF THE INVENTION

1. Field of the Invention

The present invention relates to an adjustable spinal plate, and more specifically to a spinal plate which is used to perform fixation surgery on a spine in orthopedic surgery and neurosurgery.

2. Description of the Related Art

In general, a spine forms a pillar of the body, and an upper portion thereof is a portion forming a backbone of a human body that connects an upper skull and a lower pelvis. The spine includes 7 cervical vertebrae, 12 thoracic vertebrae, 5 lumbar vertebrae, 5 sacral vertebrae, and 3 to 5 coccyges from the top. In such a spine, symptoms such as an intervertebral disc disease and lumbar herniated intervertebral disc are likely to occur by prolonged or excessive use. In general, patients having spinal disorders such as spinal fracture and dislocation are subjected to treatment and correction by fixing the respective vertebrae so as not to be moved relative to each other. For this, a spinal fixation device has been widely used for fixing the vertebrae during fusion in the art.

Such a spinal plate generally refers to an implantation plate used for treatment of the spinal disorders. The spinal implant is used for spinal fusion in which a fusion cage of an artificial implant is inserted between vertebrae from which a damaged intervertebral disk is removed due to various spinal disorders, thus to restore and maintain an interval between the vertebrae. In the conventional case, the fusion cage inserted between the vertebrae is used simultaneously with bone screws and a rod applied simultaneously to the back of the vertebral body, or is used in such a manner in which the cage is coupled and fixed by a plate and connection bolts screwed to the vertebrae, or the cage itself is equipped with bone screw holes that can be installed the bone screws to directly fix the cage to the vertebrae.

However, since spin shapes are very diverse depending on conditions of the patients during the surgery, a case in which a doctor needs to use the spinal plate by modifying the shape thereof for each situation occurs. However, it is not easy to accurately modify the shape of the spinal plate according to the various spin shapes of the patients. Therefore, when actually performing the surgery, there are problems that the spinal plate does not adhere to the vertebrae but is detached or somewhat incompletely attached, thereby side effects occur, or the surgery has to be performed again.

In addition, the patients prefer minimally invasive spine (MIS) surgery because of its potential benefits: less blood loss from surgery, reduced risk of muscle damage, reduced risk of infection and postoperative pain, faster recovery time, better cosmetic results because of relatively smaller skin incisions, etc. In order to perform MIS surgery, it is crucial that the doctors should be able to gain access to the spinal area by making as smaller skin incisions as possible and insert the spinal plate through these small skin incisions. In other words, the spinal plate, whose shape can be easily modified depending on conditions of the patients during the surgery and which can be inserted through patients' small skin incisions, is required for successful MIS surgery.

PRIOR ART DOCUMENT

Patent Document (Patent Document 1) U.S. Patent Application Publication No. US2018-0235671A (Patent Document 2) U.S. Patent Application Publication No. US2013-0060283A

SUMMARY OF THE INVENTION

An object of the present invention is to provide a spinal plate to be used by fixing any one or more of longitudinal ends of the plate with being rotated at any angle, thereby allowing a doctor to use the spinal plate by modifying a shape thereof to the shape desired by the doctor during a surgery, and to perform the surgery by coping with various spin shapes of patients.

In order to achieve the above object, according to an aspect of the present invention, there is provided a spinal plate comprising: a central body; and a pair of end bodies which are disposed on both sides of longitudinal direction of the central body and have one or more fixing screw holes in which fixing screws to be inserted into vertebrae are received, wherein at least one of the pair of end bodies includes a rotation device configured to fix the end body to the central body in a selectively rotatable manner, and a rotation locking device configured to maintain the rotation device in an unlocked state or a locked state, the rotation locking device is connected to the rotation device in the unlocked state, and the rotation locking device is integrally coupled to the rotation device by an external force, so that the movement of the rotation device is restricted, whereby the rotation device is in locked state.

Herein the rotation device includes central joints disposed on both sides in the longitudinal direction of the central body, a wing joint disposed to correspond to the central joint on one side of the wing body, and a rotation pin passing through the center joint and the wing joint, and the rotation locking device is disposed at both ends of the rotation pin.

In addition, the rotation locking device is a locking wedge installed in locking wedge insertion portions formed at both ends of the rotation pin.

Further, the locking wedge includes a wedge body, a first wedge fixing part disposed on one side of the wedge body and having a cross section wider than the wedge body, a second wedge fixing part disposed on the other side of the wedge body and having a cross section wider than the first wedge fixing part, and a wedge inclined surface disposed between the second wedge fixing part and the wedge body, the locking wedge insertion portion of the rotation pin includes pin expanding parts formed at both ends of the pin body of the rotation pin and divided into a plurality of pieces by pin slits, a first locking wedge seat formed inside the pin expanding parts in which the first wedge fixing part is seated, a stopper formed continuously to the first locking wedge seat so that the first locking wedge is not separated, and a second locking wedge seat formed continuously to the stopper and in close contact with the second wedge fixing part, and the unlocked state is a state in which the first wedge fixing part is inserted into the first locking wedge seat, and the locked state is a state in which the second wedge fixing part is forcibly inserted into the second wedge locking part by an external force to expand the pin expanding part outward.

Further, a central rotation limiting part is formed to protrude from the central joint of the central body, and a wing rotation limiting part is formed on the wing body having a shape corresponding to the central rotation limiting part so that the rotation of the wing body with respect to the central body is restricted.

Furthermore, a sliding surface and a stopping surface in contact with the rotation support surface of the central body are continuously formed in the wing joint, and the rotation of the wing body with respect to the center body is restricted while the stopping surface is in surface contact with the rotation support surface.

According to the present invention, the rotation device and the locking device may be installed so as to be used by fixing any one or more of longitudinal ends of the plate with being rotated at any angle, thereby allowing a doctor to modify a shape of the spinal plate to the shape desired by the doctor, and to perform the surgery by coping with various spin shapes of the patients.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a perspective view illustrating an adjustable spinal plate according to embodiment of the present invention;

FIG. 2 is an exploded perspective view illustrating a central body of the adjustable spinal plate according to embodiment of the present invention;

FIG. 3 is a perspective view illustrating a screw locking unit of the adjustable spinal plate according to embodiment of the present invention;

FIG. 4 is a partially enlarged perspective view illustrating a rotation pin of the adjustable spinal plate according to embodiment of the present invention;

FIG. 5 is a perspective view illustrating a locking wedge of the adjustable spinal plate according to embodiment of the present invention;

FIG. 6 is a partial cross-sectional perspective view of the adjustable spinal plate according to embodiment of the present invention;

FIG. 7 is a side view illustrating a state in which the adjustable spinal plate according to embodiment of the present invention is being inserted with being folded; and FIG. 8 is a side view illustrating a state in which the adjustable spinal plate according to embodiment of the present invention has been inserted with being unfolded.

DETAILED DESCRIPTION OF THE INVENTION

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

In FIG. 1 and FIG. 2, reference numeral 100 designates a adjustable spinal plate according to an embodiment of the present invention.

The spinal plate 100 according to the present invention basically includes a central body 102, and a pair of wing bodies 104 in which one or more fixing screw hole 144 for accommodating the fixing screws 110 to be inserted into the spine are formed.

The pair of wing bodies 104 are fixed by a rotation device so as to be rotatable with respect to the central body 102. In addition, the spinal plate 100 includes a rotation locking device for maintaining the rotation device in an unlocked state or a locked state so that the wing body 104 relative to the central body 102 can be fixed at an arbitrary angle.

One or two fixing screw holes 144 may be disposed in one wing body 104, and the fixing screw hole 144 in which an auxiliary screw 112 smaller than the fixing screw 110 can be inserted may be formed in the wing body 104 as in the embodiment of the present invention.

After the fixing screw 110 and the auxiliary screw 112 are installed on the wing body 104, a screw locking unit 108 may be additionally installed on the wing body 104 so as that the fixing screw 110 and the auxiliary screw 112 are not separated. The wing body 104 is provided with a screw fixing part seat 148 to which the screw locking unit 108 is installed.

As shown in FIG. 3, the screw locking unit 108 includes a screw fixing shaft 152 for being inserted into the screw fixing part seat 148, and a screw fixing head 150 integrally formed with the screw fixing shaft 152 and provided with a screw fixing tool groove 154 connected to a tool. A part of the circumference of the screw fixing head 150 is symmetrically formed with a screw releasing prevention part 158 formed concavely, and a screw installing part 156 formed convexly on the rest of the circumference is arranged. Therefore, by rotating the screw fixing unit 108, the fixing screw 110 and the auxiliary screw 112 can be inserted into the fixing screw hole 144 and the auxiliary screw hole 146, or in a state in which the fixing screw 110 and the auxiliary screw 112 are inserted, they are prevented from being separated from the fixing screw hole 144 and the auxiliary screw hole 146.

In the unlocked state, the rotation lock device is connected to the rotation device, and the rotation lock device is integrally coupled to the rotation device by an external force while restricting the movement of the rotation device, whereby the rotation device is in a locked state. Therefore, it is possible for the user to fix the wing body 104 to an arbitrary angle with respect to the central body 102 so as not to move any more.

The rotation device includes a central joint 126 disposed on both sides of the central body 102 in the longitudinal direction, and a wing joint 136 disposed on one side of the wing body 104 to correspond to the central joint 126, and a rotation pin 114 penetrating the center joint 126 and the wing joint 136.

A center rotating pin hole 128 is formed in the center joint 126, and a wing rotating pin hole 142 is formed in the wing joint 136. Accordingly, the rotating pin 114 passes through the center rotating pin hole 128 and the wing rotating pin hole 142 at the same time.

In addition, the rotation lock device is disposed at both ends of the rotating pin 114. The rotating locking device is a locking wedge 116 installed in a locking wedge insertion portion 166 formed at both ends of the rotating pin 114.

First, the rotating pin 114 will be described with reference to FIG. 4. lock wedge insertion portions 166 are disposed at both ends of the rotating pin 114. The lock wedge insertion part 166 includes a pin expanding part 162 formed at both ends of a pin body 160 of the rotating pin 114 and divided into a plurality of pieces by pin slits 164. In the embodiment of the present invention, four pin slits 164 and four pin expansion parts 162 are formed.

In addition, a second locking wedge seat 174 is disposed from the outermost side of the pin expanding part 162 in the space formed inside the pin expanding part 162, and the first locking wedge seat 168 is disposed continuously to the second locking wedge seat 174 to have a smaller cross-sectional area than the second locking wedge seat 174.

On the outside of the first locking wedge seat 168 in the longitudinal direction of the pin body 160, a stopper 170 is formed to have a smaller cross-sectional area than the first locking wedge seat 168. In addition, a pin inclined surface 172 is formed between the stopper 170 and the second locking wedge seat 174.

Next, the locking wedge 116 will be described with reference to FIG. 5.

A wedge body 176 of the locking wedge 116 has a cross-sectional area that can be inserted into the stopper 170. In addition, a first wedge fixing part 178 capable of being seated on the first locking wedge seat 168 is formed on one side of the wedge body 176. The first wedge fixing part 178 has a larger cross-sectional area than the stopper 170.

In addition, a wedge inclined surface 180 having a gradually enlarged cross-sectional area is formed on the other side of the wedge body 176, and a second wedge fixing part 182 larger than the cross-sectional area of the second locking wedge seat 174 is formed continuously on the wedge inclined surface 180.

That is, if the order of the cross-sectional area is arranged from small to large, the wedge body 176, the first wedge fixing part 178, and the second wedge fixing part 182 are arranged in the order.

In the unlocked state, when the first wedge fixing part 178 of the locking wedge 116 is inserted into the first locking wedge seat 168 of the rotating pin 114, the first wedge fixing part 178 is caught on the stopper 170 and cannot be separated to the outside.

When the wedge head 184, which is the outermost surface of the locking wedge 116, is pressed from the outside, the locking wedge 116 moves into the locking wedge insertion part 166 along the longitudinal direction of the pin body 160.

Further, the second wedge fixing part 182 is finally seated in the second locking wedge seat 174 while pushing the pin expanding part 162. As a result, the outer diameter of the pin expanding part 162 becomes larger than the outer diameter of the pin body 160.

The rotation pin 114 is press-fitted so as not to be rotated relative to the center rotating pin hole 128, and the rotating pin 114 has a surface contact or tolerance to enable relative rotation in the wing rotating pin hole 142.

Therefore, when the locking wedge 116 enlarges the outer diameter of the pin expanding part 162 due to an external force, the outer peripheral surface of the pin expanding part 162 strongly pushes the inner peripheral surface of the wing rotating pin hole 142 and becomes in an interference fit state. Therefore, the wing body 104 is in a locked state that does not rotate with respect to the central body 102.

It is preferable that the angle at which the wing body 104 is rotated is limited to the lower side than the straight line in the longitudinal direction of the central body 102 in order to correspond to the structure of the spine of the human body. Therefore, the sliding surface 138 and the stopping surface 140 in contact with the rotation support surface 124 of the center body 102 are continuously formed in the wing joint 136. The sliding surface 138 is disposed on the upper side of the wing joint 136, and the stopping surface 140 is disposed on the lower side of the wing joint in succession to the sliding surface 138.

Accordingly, the sliding surface 138 is in line contact with the rotation support surface 124, but the stopping surface 140 makes surface contact with the rotation support surface 124, so the wing body 104 is rotation can be restricted.

In addition, in order to reinforce the rotation restriction of the wing body 104, as shown in FIG. 6, a central rotation limiting part 130 is formed to protrude from the central joint 126 of the wing body 104, and the wing body 104 may be provided with a wing rotation limiting part 137 having a shape corresponding to the central rotation limiting part 130.

That is, while the wing body 104 rotates with respect to the central body 102, the wing body 104 by the contact between the central rotation limiting part 130 and the wing rotation limiting part 137 cannot be rotated any longer, and maintains a constant angle with respect to the central body 102.

The rotation limiting angle of the wing body 104 with respect to the center body 102 may be changed according to the intention of the designer.

The load applied to the spine plate 100 in the human body is largely a compressive load applied in the longitudinal direction of the central body 102 and a torque load having the longitudinal direction as a virtual rotational center axis.

When the compression load or torque load is transmitted to the center body 102 through the wing body 104, if the resistance to the load of the center body 102 is large, the load is concentrated on the rotation pin 114, and the rotation pin 114 may be damaged. Accordingly, the waist part 120 is formed so that the width of the central portion of the central body 102 is narrower than the width of the wing body 104, thereby reducing the resistance to the load of the central portion of the central body 102, so that the stress may be well distributed throughout the spine plate 100.

In addition, the waist part 120 may provide an extra space for the installation instrument to grip the spinal plate 100 in a narrow surgical path.

An enlarged part 122 is formed by extending in the width direction from both ends of the central body 102 in the longitudinal direction than the waist part 120. The width of the enlarged part 122 is the same as or similar to the width of the wing body 104, and the rotation support surface 124 in contact with the wing joint 136 of the wing body 104 is formed in the expanded part 122.

Additionally, a through hole 132 may be added to the center of the central body 102. Through this through hole 132, it is possible to pass the guide wire used in minimally invasive surgery. Accordingly, the position at which the spinal plate 100 is to be seated in the human body can be precisely aligned by the guide wire inserted into the through hole 132.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

According to the present invention, it is possible to use the spinal plate by modifying the shape thereof in the shape desired by the doctor during the surgery, thereby developing a spinal plate that can cope with the various spin shapes of the patients.

In addition, the shape of the spinal plate may be deformed at various angles with a single plate, it is possible to reduce the burden of preparing the plates for each operation during the surgery, thereby greatly reducing product costs from the manufacturer's point of view.

DESCRIPTION OF REFERENCE NUMERALS

100: Adjustable spinal plate
102: Central body 104, 106: Wing body
108: Screw locking unit
110: Fixing screw
112: Auxiliary screw
114: Rotating pin
116: Locking wedge
120: Waist part
122: Enlarged part
124: Rotating support part
126: Central joint
128: Central rotating pin hole
130: Central rotating limiting part
132: Through hole
136: Wing joint
137: Wing rotating limiting part
138: Sliding surface
140: Stopping surface
142: Wing rotating pin hole
144: Fixing screw hole
146: Auxiliary screw hole
148: Screw locking unit seat
150: Screw locking head
152: Screw locking shaft
154: Screw locking tool groove
156: Screw installing part
158: Screw releasing prevention part
160: Pin body
162: Pin expanding part
164: Pin slit
166: Locking wedge insertion portion
168: First locking wedge seat
170: Stopper
172: Pin inclined surface
174: Second locking wedge seat
176: Locking wedge body
178: First wedge fixing part
180: Locking wedge inclined surface
182: Second wedge fixing part
184: Locking wedge head

What is claimed is:

1. An adjustable spinal plate comprising:
a central body; and
a pair of end bodies which are disposed on both sides of a longitudinal direction of the central body and have one or more fixing screw holes in which fixing screws to be inserted into vertebrae are received,
wherein at least one of the pair of end bodies includes a rotation device configured to fix the end bodies to the central body rotatably, and a rotation locking device configured to maintain the rotation device in an unlocked state or a locked state,
the rotation locking device is connected to the rotation device in the unlocked state, and
the rotation locking device is integrally coupled to the rotation device by an external force, so that the movement of the rotation device is restricted, whereby the rotation device is in locked state,
wherein the rotation device includes central joints disposed on both sides in the longitudinal direction of the central body, a wing joint disposed to correspond to the central joint on one side of a wing body, and a rotation pin passing through the central joint and the wing joint, and the rotation locking device is disposed at both ends of the rotation pin,
wherein the rotation locking device is a locking wedge installed in locking wedge insertion portions formed at both ends of the rotation pin, and
wherein the locking wedge includes a wedge body, a first wedge fixing part disposed on one side of the wedge body and having a cross section wider than the wedge body, a second wedge fixing part disposed on the other side of the wedge body and having a cross section wider than the first wedge fixing part, and a wedge inclined surface disposed between the second wedge fixing part and the wedge body,
the locking wedge insertion portion of the rotation pin includes pin expanding parts formed at both ends of a pin body of the rotation pin and divided into a plurality of pieces by pin slits, a first locking wedge seat formed inside the pin expanding parts in which the first wedge fixing part is seated, a stopper formed continuously to the first locking wedge seat so that the locking wedge is not separated, and a second locking wedge seat formed continuously to the stopper and in close contact with the second wedge fixing part, and
the unlocked state is a state in which the first wedge fixing part is inserted into the first locking wedge seat, and the locked state is a state in which the second wedge fixing part is forcibly inserted into the second locking wedge seat by an external force to expand the pin expanding part outward.

2. The adjustable spinal plate according to claim 1, wherein a central rotation limiting part is formed to protrude from the central joints of the central body, and a wing rotation limiting part is formed on the wing body having a shape corresponding to the central rotation limiting part so that the rotation of the wing body with respect to the central body is restricted.

3. The adjustable spinal plate according to claim 1, wherein a sliding surface and a stopping surface in contact with a rotation support surface of the central body are continuously formed in the wing joint, and the rotation of the wing body with respect to the central body is restricted while the stopping surface is in surface contact with the rotation support surface.

* * * * *